United States Patent [19]

Webb, Jr. et al.

[11] Patent Number: 4,714,470
[45] Date of Patent: Dec. 22, 1987

[54] GROOVED PROSTHETIC IMPLANT

[75] Inventors: John D. Webb, Jr., Etna Green; Roy Y. Hori, Warsaw; George E. Simpson, Fort Wayne, all of Ind.

[73] Assignee: Zimmer, Inc., Warsaw, Ind.

[21] Appl. No.: 830,827

[22] Filed: Feb. 19, 1986

[51] Int. Cl.[4] ............................................. A61F 2/30
[52] U.S. Cl. ........................................ 623/18; 623/23
[58] Field of Search ...................... 623/16, 17, 18, 19, 623/20, 21, 22, 23

[56] References Cited

U.S. PATENT DOCUMENTS

| | | | |
|---|---|---|---|
| 2,718,228 | 9/1955 | Van Steenbrugghe | 128/92 |
| 3,816,854 | 6/1974 | Schlein | 3/1 |
| 3,869,731 | 3/1975 | Waugh et al. | 623/20 |
| 3,894,297 | 7/1975 | Mittelmeier et al. | 3/1 |
| 3,965,490 | 6/1976 | Murray et al. | 3/1.913 |
| 4,021,865 | 5/1977 | Charnley | 3/1.913 |
| 4,031,571 | 6/1977 | Heimke et al. | 3/1.913 |
| 4,038,703 | 8/1977 | Bokros | 623/20 |
| 4,068,324 | 1/1978 | Townley et al. | 3/1.913 |
| 4,163,292 | 8/1979 | Averett, Jr. | 3/1.913 |
| 4,177,524 | 12/1979 | Grell et al. | 623/16 |
| 4,199,824 | 4/1980 | Niederer | 3/1.913 |
| 4,259,072 | 3/1981 | Hirabayashi et al. | 433/173 |
| 4,261,063 | 4/1981 | Blanquaert | 3/1.91 |
| 4,310,931 | 1/1982 | Muller | 3/1.913 |
| 4,404,693 | 9/1983 | Zweymuller | 3/1.913 |
| 4,406,023 | 9/1983 | Harris | 3/1.912 |
| 4,407,022 | 10/1983 | Heimke et al. | 3/1.913 |
| 4,430,761 | 2/1984 | Niederer et al. | 623/23 |
| 4,495,664 | 1/1985 | Blanquaert | 3/1.913 |
| 4,520,511 | 6/1985 | Gianezio et al. | 3/1.913 |
| 4,530,116 | 7/1985 | Frey | 623/23 |
| 4,535,487 | 8/1985 | Esper et al. | 623/23 |
| 4,536,894 | 8/1985 | Galante et al. | 623/22 |
| 4,546,501 | 10/1985 | Gustilo et al. | 623/23 |
| 4,549,319 | 10/1985 | Meyer | 623/22 |
| 4,608,052 | 8/1986 | Van Kampen et al. | 623/18 |

FOREIGN PATENT DOCUMENTS

| | | | |
|---|---|---|---|
| 0011668 | 6/1980 | European Pat. Off. | 623/23 |
| 0025814 | 4/1981 | European Pat. Off. | |
| 0181586 | 4/1983 | European Pat. Off. | 623/22 |
| 0098224 | 1/1984 | European Pat. Off. | |
| 0128036 | 12/1984 | European Pat. Off. | |
| 0131178 | 1/1985 | European Pat. Off. | |
| 0169976 | 2/1985 | European Pat. Off. | 623/22 |
| 0141022 | 5/1985 | European Pat. Off. | |
| 0145939 | 6/1985 | European Pat. Off. | |
| 0176421 | 9/1985 | European Pat. Off. | 623/22 |
| 0159462 | 10/1985 | European Pat. Off. | |
| 0158534 | 10/1985 | European Pat. Off. | |
| 0158014 | 10/1985 | European Pat. Off. | |
| 2520055 | 11/1975 | Fed. Rep. of Germany | 623/18 |
| 0159035 | 2/1983 | Fed. Rep. of Germany | 623/22 |
| 989341 | 4/1902 | France . | |
| 1047640 | 12/1953 | France | 1/ |
| WO85/03426 | 8/1985 | PCT Int'l Appl. | 623/23 |

OTHER PUBLICATIONS

Protek ad—CLS Cementless Hip Stem—*JBJS*, No. 3, Mar. 1986, 68-A.
Aesculap ad—P.M. Total Hip System—*JBJS*, No. 3, Mar. 1986, 68-A.
Ostenonics Brochure—Integrated Systems of Implants and Instruments ©1984.
Joint Medical Products Brochure—S—ROM 135 TM Cementless Total Hip System—JMP-002-5M-1/85.
Richards Ad—The Bio-Fit TM Stem—JBJS vol. 67-A No. 9, Dec. 1985—Richards Medical Co.—1985.
Zimmer Brochure—The Total System—© 1984—Zimmer, Inc.

*Primary Examiner*—Richard J. Apley
*Assistant Examiner*—David J. Isabella
*Attorney, Agent, or Firm*—Margaret L. Geringer

[57] ABSTRACT

A prosthetic implant including a plurality of discrete grooves disposed in the proximal end of the implant stem. The grooves are each segments of curves generated from radii having a center of curvature offset from the implant stem in a generally lateral direction and toward the upper portion of the proximal end of the stem. The curve segments are preferably segments of concentric circles.

18 Claims, 9 Drawing Figures

4,714,470

GROOVED PROSTHETIC IMPLANT

BACKGROUND OF THE INVENTION

The present invention relates to a prosthetic implant device, and more particularly to such implants including grooved or textured surfaces. This invention is particularly suitable for use as a hip stem implant, although is not limited thereto.

Heretofore, various types of grooved, textured or porous surfaces have been incorporated into prosthetic implants. Implants are often typically affixed into bone with a grouting material, such as polymeric bone cement. In such cases, various types of grooves, texturing or porous outer surfaces enhance the bond or securing between the bone cement and the prosthesis. Other times, implants are put in without bone cement. In these cases, it is typically desirable to provide a close, tight fit between the portion of the prosthesis to be embedded in the bone and the prepared bone surface. This tight fit is provided to stabilize the prosthesis in its proper location in the bone. With many such porous or grooved or textured surfaces implanted without bone cement, after a period of time, bony ingrowth of the contacting bone surfaces occurs in and around the porous, grooved or textured surfaces to biologically affix or further secure the implant in the bone. Often, such tight fitting implants which are utilized without a grouting material such as bone cement, are referred to as press-fit implants.

The following U.S. Patents disclose prosthetic implants which include an elongated stem, each with a plurality of substantially parallel grooves which extend longitudinally and substantially in the direction of the longitudinal axis of the stem: U.S. Pat. No. 4,430,761 to Niederer et al, U.S. Pat. No. 4,404,693 to Zweymuller, U.S. Pat. No. 3,816,854 to Schlein, and U.S. Pat. No. 2,718,228 to Van Steenbrugghe. Such grooved stems as these, if used as press-fit stems, can obtain bone ingrowth in the grooves; however, their means of transferring stress to bone is primarily through shear or sliding. Bone can transmit and accept compressive forces of significantly greater magnitude than shear forces and thus, by providing a means for compressive stress transfer to the bone (as accomplished by the present invention), the long-term fixation stability of the stem will be enhanced.

U.S. Pat. No. 4,530,116 to Frey discloses a hip stem which includes dimples or indents over the surface of the stem, while U.S. Pat. No. 4,068,324 to Townley et al discloses a hip stem which includes projecting steps.

In addition, various types of porous surfaces have been included on prosthetic implants to either enhance the securement between the bone cement/prosthesis interface when used with cement, or when used without cement or the like, the porous surfaces promote the ingrowth of bone to enhance the secure fixation of the prosthesis to the bone. U.S. Pat. No. 4,536,894 to Galante et al discloses a hip prosthesis including porous fiber metal pads on its fixation surface, while European Patent EP No. 0 128 036 to Kenna discloses a hip stem including a porous beaded fixation surface.

OBJECTS OF THE INVENTION

A principle object of this invention is to provide a prosthetic joint implant device which is suitable for use as a press-fit implant and which includes a grooved configuration which provides good proximal stress transfer of the joint forces from the stem to the bone.

Another object of the invention is to provide a prosthetic stemmed implant such that, if removal of the stem becomes necessary, the major fixation grooves are all proximally located, and thus accessible to instruments for breaking the bone/stem bond (when used as a press-fit implant without cement), and thus permitting removal of the stem.

A further object of the invention is to provide a prosthetic joint implant which is suitable for an optimal press-fit within the prepared bone cavity.

A still further object of the invention is to provide a grooved prosthetic joint implant which is suitable for press-fit implantation, such grooves being able to rasp or cut bone upon implantation. It is an object of the invention to provide such grooves as "self-bone grafting" grooves, thus the bone chips from the rasped bone naturally collect and fill each groove to enhance and accelerate the process by which the stem can become ingrown with bone and thus well fixed in the bone when used as a press-fit implant.

SUMMARY OF THE INVENTION

The present invention provides a prosthetic implant which includes a plurality of discrete grooves disposed in the proximal end of the implant stem. The grooves are each segments of curves preferably generated from radii having a center of curvature offset from the implant stem in a generally lateral direction and toward the upper portion of the proximal end of the stem. The curved segments are preferably segments of concentric circles.

The grooves each have a cross-sectional configuration including a sharp projecting superior edge, a connecting base, and a sloped inferior edge. The sharp superior edge can cut bone during the insertion process. As the sharp edges cut bone, the bone chips naturally collect into and fill each groove. Therefore, the grooves may be termed "self-bone grafting" grooves. The inferior sloped edge of the groove has the opposite effect of the sharp superior edge. Should the stem need to be removed, the sloped inferior edge of each groove will provide less resistance and facilitate stem removal.

BRIEF DESCRIPTION OF THE DRAWINGS

These features and objects of the invention, as well as others, will become apparent to those skilled in the art by referring to the accompanying drawings.

DETAILED DESCRIPTION OF THE INVENTION

FIGS. 1-9 illustrate a particularly advantageous embodiment of a grooved prosthetic implant according to the present invention. The invention will be described with reference to a hip prosthesis implant and is particularly suitable as such. However, it is understood that the principles of the invention may be suitable for other implants having elongated fixation stems. In addition, the hip implant will primarily be described in reference to its primary intended use as a press-fit (non-cemented) hip stem. However, it is understood that the principles of the grooved implant stem could also be utilized on a cemented prosthesis to enhance the fixation between the prosthesis and the cement.

Figure 1:
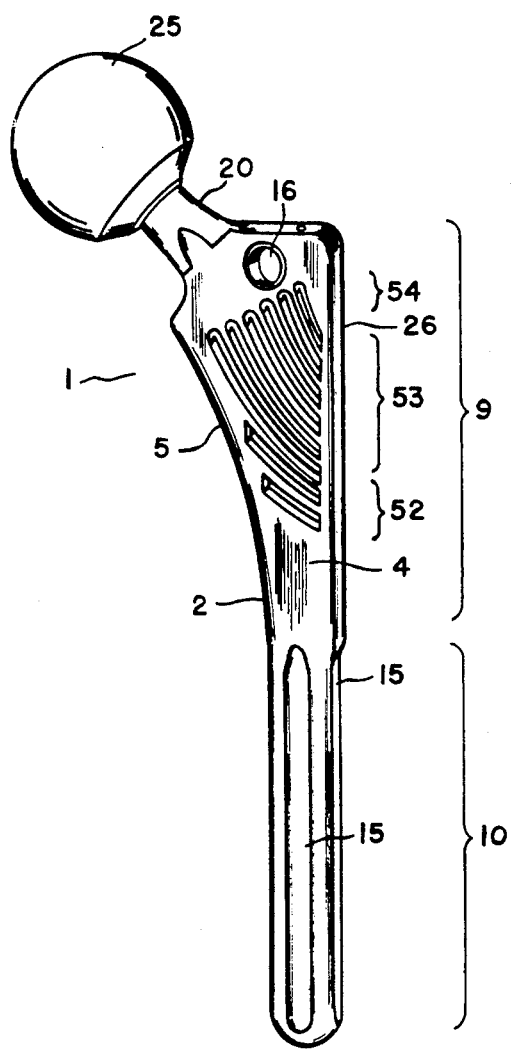
FIG. 1 is a perspective view of a hip stem implant according to the present invention.
Figure 2:
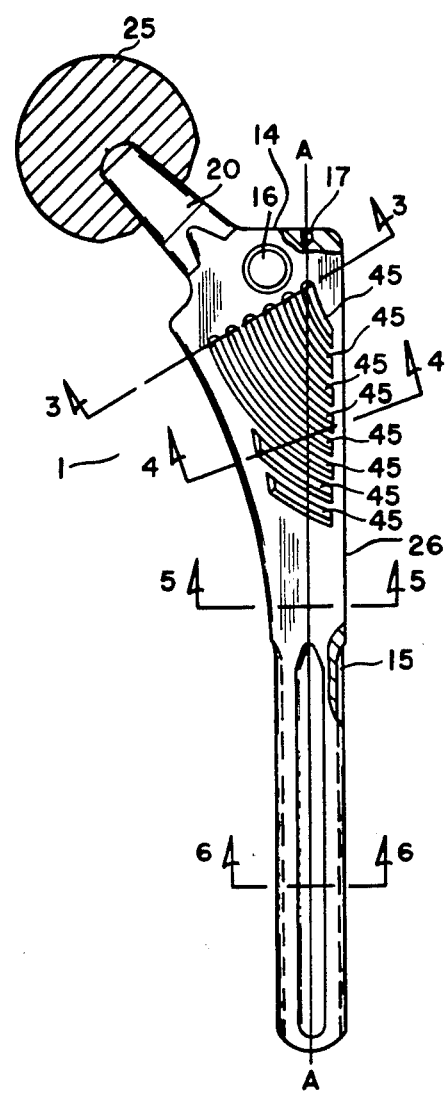
FIG. 2 is a side elevation view of the hip stem shown in partial cross-section.

The prosthetic hip implant 1 of FIG. 1 includes a head 25 and a stem 26. The head 25 may be integrally formed with the stem 26 or it may be a separate component from the stem, such as is shown in FIGS. 1 and 2. The stem 26 includes a proximal end 9 and a distal end 10. Generally, the proximal end 9 is considered to be approximately the top half portion of the stem 26, and the distal end 10 is considered to be approximately the bottom half portion of the stem 26. The stem 26 includes a pair of approximately opposite sidewalls 4 separated by a medial side 2 and a lateral side 3. The lateral side 3 is substantially parallel to the longitudinal median axis A—A of the stem 26. The distal end 10 of the medial side 2 is also substantially parallel to axis A—A and then blends into an arcuate portion 5 which curves away from axis A—A to form the wider proximal portion 9.

Figure 7:
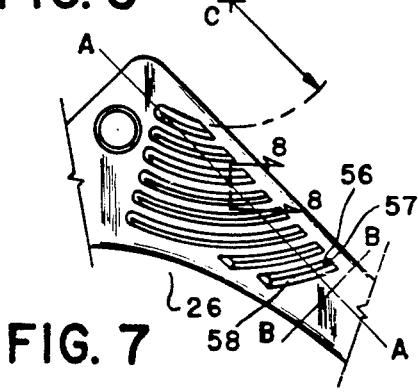
FIG. 7 is a partial side elevation view of the hip stem.

The sidewalls 4 include a plurality of discrete grooves 45 arcuately disposed at the proximal end 9 of the stem 26. The grooves 45 are each segments of curves generated from radii having a center of curvature offset from the stem 26 in a generally lateral direction and generally toward the upper portion of the proximal end 9 of the stem 26. The grooves are preferably segments of concentric circles having their center of radius "c," as shown in FIG. 7.

Figure 8:
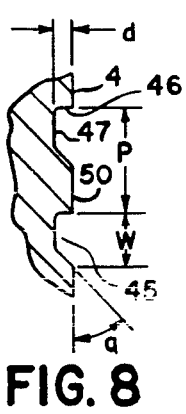
FIG. 8 is a partial cross-sectional view of the hip stem taken along lines 8—8 of FIG. 7.

The grooves 45 each have a cross-sectional configuration, as shown in FIG. 8 which includes a sharp projecting superior edge 46, a connecting base 47, and a sloped inferior edge 48.

The superior edge 46 of each groove has a sharp projecting edge. This sharp edge is capable of cutting bone during the insertion process. In profile, the superior edge 46 projects at an angle of approximately 90° to the sidewall 4. It is noted that the implant stem 26 is generally oversize compared with the corresponding rasp instrument (not shown) used to prepare the opening in the femoral canal. Thus, as the implant stem 26 is being seated in the femoral canal, the grooves 45 in the stem 26 perform a final rasping function, thus form fitting the stem 26 to the femoral cavity in order to provide an optimal press-fit. As the sharp superior edges 46 cut bone upon insertion of the implant stem 26, the resulting bone chips naturally collect into and fill each groove 45, thus the grooves 45 may be termed "self-grafting." This self-grafting feature greatly enhances and accelerates the process by which the stem 26 can become ingrown with bone and thus well fixed in the femur.

The inferior edge 48 of each groove is sloped at an angle "a." This angle "a" is preferably 45°, although it could suitably range from between approximately 20° to 60° measured from the sidewall 4. This slope of the inferior edge 48 has the opposite effect of the sharp superior edge 46. Should the stem 26 need to be removed, the sloped inferior edge 48 of each groove 45 will provide less resistance and facilitate removal of the stem 26.

Each groove 45, in cross-section, is substantially a three-sided figure with the open side open to bone. When considering the superior edge 46, the connecting base 47 and the inferior edge 48 in three dimensions, the superior edge 46 forms a superior face 56, the connecting base 47 forms a base surface 57 and the inferior edge 48 forms an inferior face 58. The superior face 56 forms a flat portion. When a groove 45 of an implanted stem 26 has become ingrown with bone, this flat portion provides for direct compressive forces to be applied to the bone. This provides for good stress transfer from a prosthesis stem 26 to bone. Compressive forces are preferred over simple shear or sliding forces in transmitting force to bone.

The base surface 57 of each groove 45 is substantially flat rather than curved or rounded. The base surface 57 is approximately parallel to the sidewall 4. This flat base shape has a reduced stress concentration effect, and thus helps to maintain the high strength of the femoral stem 26 itself. There are small filets at the corners between the base surface 57 on the grooves 45 and the superior and inferior faces 56 and 58. Even though these corner filets have a smaller radius than would be possible if the entire base surface 57 of the groove 45 was curved, the combined effect of the small filets and flat at the groove base surface 57 is to provide a reduced stress concentration factor over that which would be seen if the base surface 57 of the groove 45 was simply curved.

Referring to FIG. 8, the grooves 45 typically range in width "w" from 1 mm to 4 mm and in depth "d" from 0.25 mm to 1 mm. Optimally, the grooves 45 are approximately 2.4 mm wide and 0.75 mm deep. These grooves 45 are considered relatively large in size and may be referred to as macrogrooves which obtain macrointerlock with bone.

There are flats or lands 50 between each groove 45. These lands 50 may range in width ("p" minus "w") from approximately 0.75 to 4 mm, with "p" being the period of the grooves 45 or the distance from the beginning of one groove 45 to the beginning of another, and with "w" being the width of the opening of the groove 45. These flats or lands 50 help to provide the overall shape to the stem 26 and bear upon the sides of the bone cavity in order to obtain a press-fit.

The plurality of grooves 45 may be approximately, separated into a lower section 52, a median section 53 and an uppermost section 54. The lower section 52 of grooves 45 crosses the longitudinal median axis A—A approximately horizontally at about 0° to 15° measured from line B—B which is perpendicular to the longitudinal median axis A—A as seen in FIGS. 1 and 7. The median section 53 crosses the longitudinal axis A—A at about 35° to 55°, preferably 45°, measured from the perpendicular line B—B. The uppermost section 54 of the grooves 45 are tilted from the proximal medial to the distal lateral direction, as shown in FIGS. 1, 2, and 7.

The grooves 45 are placed or situated as described above, so as to resist motion of the stem 26 in the femur and thus provide stability of the stem 26. The lower section 52 of the grooves are almost horizontal because this portion of the femoral stem 26 will tend to settle straight down the femoral canal. These substantially horizontal grooves 45 are approximately perpendicular to the direction of motion, and thus are optimally situated to resist stem settlement as well as provide good stress transfer to bone. The median section 53 of grooves 45 are curved to the approximate 45° angle discussed above because the most proximal portion of this stem tends to tilt medially. That is, the stem tends to tilt into a varus position. The approximate 45° angle of the grooves 45 again, is perpendicular to the direction of this tilting motion, and thus are optimally situated to resist this tendency toward varus drift. The uppermost section 54 of the grooves 45 are tilted or slope from proximal medial to the distal lateral direction. As the stem 26 is being driven into the femur, this particular tilt of the grooves 45 will tend to drive the stem 26 in a lateral direction in the femur, thus helping to maintain proper alignment of the stem 26 and preventing a varus position. Varus position of femoral stems has been associated with stem fractures and stem failures, and so should be avoided.

Figure 9:
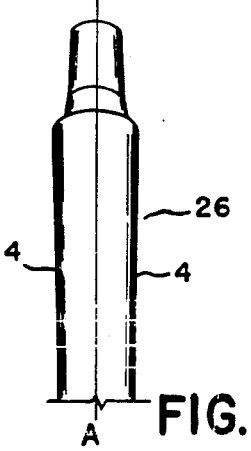
FIG. 9 is a partial near elevation view of the hip stem.

The arcuate portion 5 provides a wedge-shaped proximal end 9. The stem 26 also has a slight wedge shape as shown in FIG. 9, such that the portion of the sidewalls 4 in the proximal end 9, although substantially flat, planar surfaces, are preferably not exactly parallel planes, but rather gradually angle slightly inward toward each other as the sides 4 progress toward the distal end. This slight angle of the sidewalls 4 may be approximately 1°. This wedge shape enables each successive groove 45 to project out a little more than the groove 45 immediately below it. Thus, as the stem 26 is being driven into bone, each of the grooves 45 engages bone.

The configuration and arrangement of grooves 45 of FIGS. 1-7 which are provided in the proximal end 9 of both of the pair of opposite sidewalls 4 in the stem 26 provide advantageous results. The proximal placement of grooves 45 provides good proximal stress transfer of the femoral joint forces from the stem 26 to the proximal femoral bone. Also, should removal of the stem 26 become necessary, the major fixation grooves 45 are all proximally located, and are thus accessible to instruments for breaking the bone/stem bond, thus permitting removal of the stem.

The stem 26 as shown in FIGS. 1-7 does not include a collar portion. However, the stem 26 of the present invention could include a collar, if desirable. A collar, such as is known in the art as a calcar collar, may project directly from the medial side 2 of the stem 26 just below the transition to the neck 20 of the stem 26. By providing only a medially projecting collar, access to the grooves 45 on the pair of sides 4 is still possible. This access is necessary so that the stem/bone bond can be broken with a suitable instrument should stem removal be necessary.

In the uppermost portion of the proximal end 9, a thru hole 16 may be provided to engage a suitable instrument in order to facilitate stem extraction, as is known in the art. This extraction hole 16 can also be used in conjunction with a pin-like instrument to help control the rotation of the stem 26 during insertion or implanation.

A superior shoulder 14 is provided on the stem 26, as shown in FIGS. 1-2. The shoulder 14 may be utilized as a driving platform and includes a dimple or indent 17. This indent 17 is colinear and coincident with the center line or longitudinal axis A—A of the femoral stem 26. The indent 17 is engaged by a suitable driving instrument upon insertion of the stem 26 into the femoral canal. The driving instrument, when placed in the indent, can permit the surgeon to drive the stem 26 straight down the femoral canal without causing the stem to take on a varus position.

The distal end 10 of the stem 26, as shown in FIGS. 1-2, is substantially straight and cylindrical. Four flutes 15 may be provided to help provide rotational stability and permit endosteal revascularization of the femoral canal.

Figure 3:
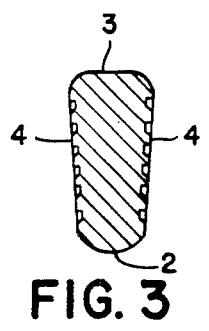
FIG. 3 is a cross-sectional view of the hip stem taken along lines 3—3 of FIG. 2.
Figure 4:
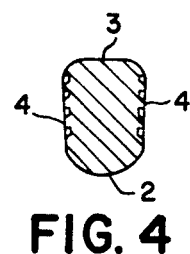
FIG. 4 is a cross-sectional view of the hip stem taken along lines 4—4 of FIG. 2.
Figure 5:
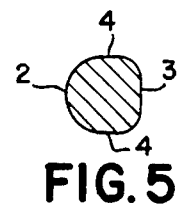
FIG. 5 is a cross-sectional view of the hip stem taken along lines 5—5 of FIG. 2.
Figure 6:
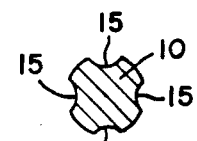
FIG. 6 is a cross-sectional view of the hip stem taken along lines 6—6 of FIG. 2.

In the proximal end 10 of the stem the lateral side 3 is substantially a smooth flat surface, while the medial side 2 is substantially a smooth convex surface, as shown in FIGS. 3-5.

A neck 20 is provided connecting the main portion of the stem 26 to the head 25. The neck 20 may be suitably provided at an angle of approximately 135° to the longitudinal axis A—A to provide an anatomical neck angle.

When the femoral implant 1 is utilized with a separate head member 25, a taper fit may be suitably provided on the neck 20 and mating head 25 to provide a taper lock therebetween. A 6° taper is suitable for this purpose. When a separate head member 25 is to be utilized, as shown, the surgeon may select the appropriate size and style of head 25 desired. Alternatively, the head 25 could be integrally formed on the neck to form a single piece (not shown) femoral implant 1.

Various sizes of steps 26 may be provided as is typical in the area of joint replacement. Stem lengths may vary with stem size ranging from about 130 mm to 175 mm in order to match anatomical variations found in femurs. The lengths of femoral necks 20 also typically increase with stem size in order to accommodate anatomical variations.

The prosthetic implant 1 may be made out of any suitable biologically acceptable implant material. Examples of such suitable materials are Titanium alloy or Cobalt-chromium alloy, although other suitable materials may be used.

The prosthetic implant of the present invention described herein includes grooves which are unique and designed to obtain macrointerlock between bone and the prosthesis stem while minimizing the stress concentration effect of the grooves on the stem itself. Thus, the overall strength of the stem is minimally compromised. While this invention has been described and exemplified, in terms of a particularly advantageous embodiment, those skilled in the art can appreciate that modifications can be made without departing from the spirit and scope of this invention.

We claim:

1. A prosthetic implant including a stem having a proximal end and a distal end and a pair of sidewalls each including a plurality of discrete grooves arcuately disposed at the proximal end of the stem wherein the stem further includes a medial side and a lateral side separating the pair of sidewalls, and wherein the plurality of grooves are each segments of curves generated from radii having a center of curvature offset from the stem in a generally lateral direction.

2. The prosthetic implant of claim 1 wherein the proximal end has an upper portion and a lower portion and wherein the center of curvature is offset from the stem in a generally lateral direction and generally toward the upper portion of the proximal end of the stem.

3. The prosthetic implant of claim 1 wherein said grooves each have a cross-sectional configuration including a sharp projecting superior edge, a connecting base, and a sloped inferior edge.

4. The prosthetic implant of claim 3 wherein the superior edge forms a flat superior face and the connecting base forms a flat base surface and the inferior edge forms an angled flat face.

5. The prosthetic implant of claim 3 wherein the grooves are separated by flat land portions.

6. The prosthetic implant of claim 3 wherein the inferior edge of each groove is sloped at an angle from between approximately 20° to 60° to the sidewalls.

7. The prosthetic implant of claim 3 wherein the inferior edge of each groove is sloped at an angle of approximately 45° to the sidewalls.

8. The prosthetic implant of claim 3 wherein the superior edge of each groove projects at an angle of approximately 90° to the sidewalls.

9. The prosthetic implant of claim 3 wherein the connecting base of each groove is approximately parallel to the sidewalls.

10. The prosthetic implant of claim 1 wherein the grooves have a depth of approximately 0.25 mm to 1 mm.

11. The prosthetic implant of claim 1 wherein the grooves have a width of approximately 1 mm to 4 mm.

12. The prosthetic implant of claim 5 wherein the land portions have a width of approximately 0.75 mm to 4 mm.

13. The prosthetic implant of claim 1 wherein the segments of curves are segments of concentric circles.

14. A prosthetic implant including a stem having a proximal end and a distal end and a pair of sidewalls each including a plurality of discrete grooves disposed at the proximal end of the stem, each groove having a cross-sectional configuration including a sharp projecting superior edge, a connecting base, and a sloped inferior edge, wherein the grooves are arcuately disposed at the proximal end of the stem and wherein the stem further includes a medial side and a lateral side separating the pair of sidewalls, and wherein the proximal end has an upper portion and a lower portion and wherein the plurality of grooves are each segments of curves generated from radii having a center of curvature offset from the stem in a generally lateral direction and toward the upper portion of the proximal end of the stem.

15. A prosthetic implant including a stem having a proximal end and a distal end and a pair of sidewalls, each sidewall including a plurality of grooves disposed at the proximal end of the stem and wherein the stem includes a longitudinal median axis extending from the proximal end through the distal end and wherein the plurality of grooves collectively includes a lower section, a median section and an uppermost section, wherein the lower section of the grooves crosses the longitudinal median axis approximately horizontal at about 0° to 15° measured from a line perpendicular to the median axis, and wherein the median section of grooves crosses the longitudinal median axis at about 35° to 55° measured from the perpendicular line, and wherein the uppermost section of the grooves are tilted from the proximal medial to the distal lateral direction.

16. The prosthetic implant of claim 15 wherein the grooves are each portions of curved segments arcuately located on the proximal portion of the stem.

17. A prosthetic implant including a stem having a proximal end and a distal end and a pair of sidewalls, each sidewall including a plurality of discrete grooves disposed at the proximal end of the stem, and wherein the stem includes a longitudinal median axis extending from the proximal end through the distal end and wherein the plurality of grooves obliquely cross the longitudinal median axis, wherein the stem further includes a medial side and a lateral side disposed between the two sidewalls, and wherein the oblique grooves slope upwardly toward the medial side of the proximal end, and wherein the plurality of grooves are segments of curves having their center of curvature offset in the lateral direction from the stem.

18. A prosthetic implant including a stem having a proximal end and a distal end and a pair of sidewalls each including a plurality of discrete grooves disposed at the proximal end of the stem wherein the stem further includes a medial side and a lateral side separating the pair of sidewalls, and wherein the plurality of grooves each include an arcuate segment generated from a radius having a center of curvature offset from the stem in a generally lateral direction.

* * * * *